United States Patent [19]

Torii et al.

[11] Patent Number: 4,933,444
[45] Date of Patent: Jun. 12, 1990

[54] PROCESS FOR PREPARING 2β-SUBSTITUTED-METHYLPENICILLIN DERIVATIVES

[75] Inventors: Sigeru Torii; Hideo Tanaka, both of Okayama; Motoaki Tanaka, Honjyo; Shozo Yamada, Tokushima; Akira Nakai, Honjyo; Hisashi Ohbayashi, Koganei, all of Japan

[73] Assignees: Taiho Pharmaceutical Co., Ltd., Tokyo; Otsuka Kagaku Kabushiki Kaisha, Osaka, both of Japan

[21] Appl. No.: 371,230

[22] Filed: Jun. 26, 1989

Related U.S. Application Data

[63] Continuation of Ser. No. 123,632, Nov. 23, 1987, abandoned.

[30] Foreign Application Priority Data

Dec. 3, 1986 [JP] Japan ................................. 61-289595
Jan. 14, 1987 [JP] Japan ..................................... 62-6759
Jun. 26, 1987 [JP] Japan ................................. 62-160278
Aug. 11, 1987 [JP] Japan ................................. 62-201536

[51] Int. Cl.$^5$ ........................................... C07D 499/04
[52] U.S. Cl. ..................................... 540/313; 540/304; 540/315; 540/338
[58] Field of Search ................. 540/304, 313, 315, 338

[56] References Cited

U.S. PATENT DOCUMENTS 4,529,592  7/1985  Micetich et al. ............... 540/310 X
4,562,073  12/1985  Micetich et al. ............... 540/310 X
4,668,514  5/1987  Micetich et al. ............... 540/310 X

FOREIGN PATENT DOCUMENTS 0110826  6/1984  European Pat. Off. .

Primary Examiner—Werren B. Lone
Assistant Examiner—Vera C. Clarke
Attorney, Agent, or Firm—Armstrong, Nikaido, Marmelstein, Kubovcik & Murray

[57] ABSTRACT

Disclosed is a process for preparing 2β-substituted-methylpenicillin derivative of the formula

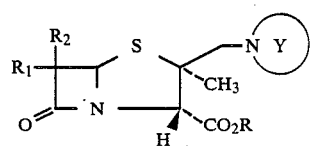

(I)

wherein R is H or carboxyl protecting group, $R_1$ is H or halo, $R_2$ is H, lower alkyl, lower alkoxy, halogen, azido, lower alkylthio, phthalimide or a group —$NHR_3$ (wherein $R_3$ is H or acyl), and —N Y is an optionally substituted monocyclic or bicyclic heterocyclic group having 1 to 4 nitrogen atoms in the ring structure, the process comprising reacting a compound of the formula

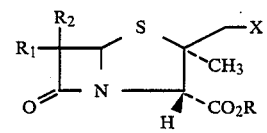

(II)

wherein X is Cl or Br, and R, $R_1$ and $R_2$ are as defined above with a heterocyclic compound of the formula

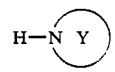

(III)

wherein —N Y is as defined above.

11 Claims, No Drawings

PROCESS FOR PREPARING 2β-SUBSTITUTED-METHYLPENICILLIN DERIVATIVES

This is a continuation of application Ser. No. 123,632, filed Nov. 23, 1987, now abandoned.

The present invention relates to a novel process for preparing a 2β-substituted-methylpenicillin derivative and more particularly to a process for preparing the same which process is capable of introducing various heterocyclic groups into the 2β-methyl group.

This invention concerns with a process for preparing a 2β-substituted-methylpenicillin derivative represented by the formula (I)

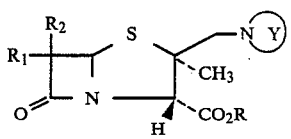

wherein R is hydrogen or a penicillin carboxyl protecting group, $R_1$ is hydrogen or halogen, $R_2$ is hydrogen, lower alkyl, lower alkoxy, halogen, azido, lower alkylthio, phthalimide or a group —$NHR_3$ (wherein $R_3$ is hydrogen or acyl), and —N Y is an optionally substituted monocyclic or bicyclic heterocyclic group having 1 to 4 nitrogen atoms as the hetero atom in the ring structure.

Substituted compounds in which a nitrogen-containing heterocyclic group is attached to the 2β-methyl group of penicillin derivatives are disclosed in U.S. Pat. Nos. 4,529,592, 4,562,073 and 4,668,514. However, these patents merely describe the compounds which have only substituted or unsubstituted 1,2,3-triazol-1-yl group as such nitrogen-containing heterocyclic group. Such substituted compounds are prepared by the following processes described in the patents.

Described therein are processes for preparing 2β-substituted-methylpenicillin derivatives comprising reacting a compound represented by the formula (IV)

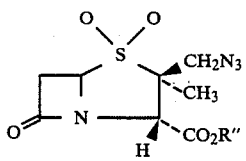

wherein R'' is a penicillin carboxyl protecting group with an acetylene derivative or a vinyl derivative which can react with the azido group of the compound of the formula (IV) to form a substituted or unsubstituted 1,2,3-triazol-1-yl group.

However, the disclosed processes can introduce only a limited range of heterocyclic groups, i.e., only substituted or unsubstituted 1,2,3-triazol-1-yl groups, and are incapable of introducing other types of heterocyclic group to the 2β-methyl group of penicillin derivatives.

An object of the invention is to provide a process by which a wide variety of heterocyclic groups can be introduced into the 2β-methyl group of penicillin compounds.

The above object and other features of the invention will become apparent from the following description.

The present invention provides a process for preparing a 2β-substituted methylpenicillin derivative represented by the formula

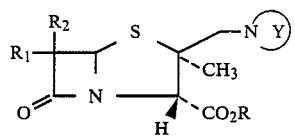

wherein R is hydrogen or a carboxyl protecting group, $R_1$ is hydrogen or halogen, $R_2$ is hydrogen, lower alkyl, lower alkoxy, halogen, azido, lower alkylthio, phthalimide or a group —$NHR_3$ (wherein $R_3$ is hydrogen or acyl), and —N Y is an optionally substituted monocyclic or bicyclic heterocyclic group having 1 to 4 nitrogen atoms as hetero atoms in the ring structure, the process comprising reacting a compound represented by the formula

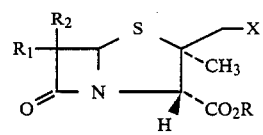

wherein X is chlorine or bromine, and R, $R_1$ and $R_2$ are as defined above with a heterocyclic compound represented by the formula

wherein —N Y is as defined above.

To overcome the foregoing prior art problem, we conducted extensive research, and found that a wide variety of 2β-substituted-methylpenicillin derivatives of the formula (I) which can have various heterocyclic group on the 2β-methyl group can be prepared by a simple step of reacting a heterocyclic compound of the formula (III) directly with a 2β-halogeno-substituted-methylpenicillin derivative represented by the formula (II). The present invention has been accomplished based on this novel finding.

The compounds of the formula (I) obtained according to the present invention are useful as intermediates for producing antibiotics and also as intermediates for preparing β-lactamase inhibitors.

Throughout the specification and claims, the nitrogen-containing heterocyclic ring groups represented by the group —N Y include 5-membered monocyclic heterocyclic ring groups having 1 to 4 nitrogen atoms in the ring structure, such as pyrrolyl, imidazolyl, pyrazolyl, tetrazolyl, 1,2,3-triazolyl, 1,2,4-triazolyl and the like; and bicyclic heterocyclic ring groups, particularly those wherein a 5-membered heterocyclic group containing 2 or 3 nitrogen atoms in its ring structure is fused with a benzene ring, such as benzotriazolyl, benzimidazolyl and the like or those wherein a 5-membered heterocyclic group containing 1 or 2 nitrogen atoms in its ring structure is fused with a 6-membered heterocyclic ring containing 1 or 2 nitrogen atoms in its ring structure, such as purinyl and the like, etc. These monocyclic and bicyclic heterocyclic ring groups may optionally have 1 to 3, preferably 1 or 2, substituents selected from the group consisting of alkyl, alkoxy, hydroxyl, halogen, nitro, amino, alkoxycarbonyl, formyl, benzyloxycarbonyl, aryl and aralkyl; the benzyloxycarbonyl optionally having 1 to 3 substituents selected from the group consisting of $C_1$-$C_6$ alkyl, halogen and nitro on the benzene ring, and the aryl being optionally substituted with 1 to 3 $C_1$-$C_6$ alkyl groups on the benzene ring. In connection with the substituents of the heterocyclic ring groups, examples of alkyl groups are straight- or branched-chain $C_1$-$C_6$ alkyl group such as methyl, ethyl, propyl, isproyl, butyl, sec-butyl, tert-butyl, pentyl, hexyl and the like. Examples of alkoxy groups are $C_1$-$C_6$ alkoxy groups such as methoxy, ethoxy, propoxy, butoxy and the like. Examples of halogen atoms are chlorine, bromine, iodine and the like. Examples of alkoxycarbonyl groups are $C_2$-$C_7$ alkoxycarbonyl groups such as methoxycarbonyl, ethoxycarbonyl, propyloxycarbonyl, isopropyloxycarbonyl, butoxycarbonyl, sec-butoxycarbonyl, tert-butoxycarbonyl, pentyloxycarbonyl and hexyloxycarbonyl and the like. Examples of benzyloxycarbonyl groups which may optionally have 1 to 3 substituents selected from the group consisting of $C_1$-$C_6$ alkyl, halogen and nitro on the benzene ring are benzyloxycarbonyl, o-nitrobenzyloxycarbonyl, p-nitrobenzyloxycarbonyl, m-nitrobenzyloxycarbonyl, p-chlorobenzyloxycarbonyl, m-chlorobenzyloxycarbonyl, o-fluorobenzyloxycarbonyl, p-bromobenzyloxycarbonyl, o-methylbenzyloxycarbonyl, p-ethylbenzyloxycarbonyl, m-propylbenzyloxycarbonyl, 4-nitro-2-methylbenzyloxycarbonyl, 2-nitro-4-ethylbenzyloxycarbonyl, 2,4-dinitrobenzyloxycarbonyl, 2,4,6-trinitrobenzyloxycarbonyl, 2,4-dimethylbenzyloxycarbonyl, 2,4,6-triethylbenzyloxycarbonyl and the like. Examples of aryl groups optionally substituted with 1 to 3 alkyl groups having 1 to 6 carbon atoms on the benzene ring are phenyl groups optionally substituted with 1 to 3 $C_1$-$C_6$ alkyl groups, such as phenyl, tolyl, xylyl and the like. Examples of aralkyl groups are $C_1$-$C_6$ alkyl groups substituted with 1 to 3 aryl groups, particularly $C_1$-$C_6$ alkyl groups substituted with 1 to 3 phenyl groups such as benzyl, phenylethyl, diphenylmethyl, trityl and the like, etc.

Examples of the penicillin carboxyl protecting groups represented by R include known groups such as any of those described in Japanese Unexamined Patent Publication No. 49-81380 and in "Cephalosporins and Penicillins, Chemistry and Biology" edited by H. E. Flynn (published in 1972 by Academic Press). Preferable examples of the group R are substituted or unsubstituted alkyl groups such as methyl, ethyl, propyl, butyl, tert-butyl and trichloroethyl; substituted or unsubstituted aralkyl groups such as benzyl, diphenylmethyl, trityl, p-nitrobenzyl and p-methoxybenzyl; acyloxyalkyl groups such as acetoxymethyl, acetoxyethyl, propionyloxyethyl, pivaloyloxymethyl, pivaloyloxyethyl, pivaloyloxypropyl, benzoyloxymethyl, benzoyloxyethyl, benzylcarbonyloxymethyl and cyclohexylcarbonyloxymethyl; alkoxyalkyl groups such as methoxymethyl, ethoxymethyl and benzyloxymethyl; and lactone such as 3-phthalidyl, crotonolacton-4-yl and γ-butyrolacton-4-yl; substituted or unsubstituted phenyl groups such as phenyl, tolyl, methoxyphenyl, nitrophenyl and the like; other groups such as (2-oxo-1,3-dioxoden-4-yl)methyl, (5-methyl-2-oxo-1,3-dioxoden-4-yl)methyl, (5-phenyl-2-oxo-1,3-dioxoden-4-yl)methyl, tetrahydropyranyl, dimethylaminoethyl, dimethylchlorosilyl, trichlorosilyl, tert-butyldimethylsilyl and the like.

Examples of halogen atoms represented by $R_1$ and $R_2$ are chlorine, bromine and the like. Examples of lower alkyl groups represented by $R_2$ are alkyl groups having 1 to 6 carbon atoms such as methyl, ethyl, propyl, butyl, tert-butyl, pentyl, hexyl and the like. Examples of lower alkoxy groups represented by $R_2$ are alkoxy groups containing 1 to 6 carbon atoms such as methoxy, ethoxy, propoxy, butoxy and the like. Examples of lower alkylthio groups represented by $R_2$ are $C_1$-$C_6$ alkylthio groups such as methylthio, ethylthio, propylthio, butylthio, hexylthio and the like.

Usable as the acyl group represented by $R_3$ are straight chain or branched chain, cyclic or acyclic acyl groups formed by removing a hydroxy group from the carboxyl group of an organic carboxylic acid optionally containing an unsaturated bond, nitrogen atom, oxygen atom, sulfur atom or the like. Examples of such acyl groups are those constituting the acylamino groups substituted at the 6-position of various conventional penicillin derivatives or at the 7-position of various conventional cephalosporin derivatives. Stated more specifically, the above organic carboxylic acids include fatty acids having 1 to 6 carbon atoms; aromatic and heterocyclic carboxylic acids wherein an aromatic residue or heterocyclic residue is attached directly to the carboxyl group; those wherein a straight- or branched-chain or cyclic saturated or unsaturated aliphatic carboxylic acid optionally containing oxygen or sulfur atom in its chain structure is linked with an aromatic hydrocarbon residue or hetrocyclic group with or without oxygen or sulfur atom existing therebetween, such as aromatic hydrocarbon residue-substituted aliphatic carboxylic acids, aromatic hydrocarbon-oxy residue-substituted aliphatic carboxylic acids, aromatic hydrocarbon-thio residue-substituted aliphatic carboxylic acids, heterocyclic group-substituted aliphatic carboxylic acids, heterocyclic-oxy group-substituted aliphatic carboxylic acids, heterocyclic-thio group-substituted aliphatic carboxylic acids and the like. Exemplary of such aliphatic carboxylic acids are straight chain and branched chain aliphatic carboxylic acids having 1 to 10 carbon atoms or cyclic aliphatic carboxylic acids having 6 to 8 carbon atoms such as formic acid, acetic acid, propionic acid, butanoic acid, isobutanoic acid, pentanoic acid, isopentanoic acid, hexanoic acid, cyclohexanecarboxylic acid, acrylic acid, crotonic acid, cyclohexylacetic acid, cyclohexenylacetic acid, methoxyacetic acid, ethoxyacetic acid, cyclohexyloxyacetic acid, methylthioacetic acid and the like. Representative of the aromatic hydrocarbon residues in the acyl groups herein are phenyl, naphthyl and the like. Illustrative of the heterocyclic groups in the acyl groups herein are saturated or unsaturated monocyclic and polycyclic, particularly bicyclic, heterocyclic groups containing at least one hetero atom, preferably 1 to 4 hetero atoms such as oxygen, sulfur or nitrogen in the ring structure, such as thiophene, furan, pyridine, pyrimidine, oxazole, pyrrole, pyrazole, imidazole, triazole, thiazole, isothiazole, isoxazole, thiadiazole, oxadiazole, tetrazole and like. The aliphatic moiety constituting the above aliphatic carboxylic acid, said aromatic hydrocarbon residue and said hetrocyclic group may optionally have at least one substituent, particularly 1 to 3 substituents, at an optional position which substituent or substituents do not participate in the reaction, examples of such substituents being halogen atoms such as fluorine, chlorine, bromine, iodine and the like, hydroxyl, amino, nitro, cyano, sulfonic acid group ($-SO_3H$), carboxyl, $C_1$–$C_6$ alkyl, $C_1$–$C_6$ alkoxy, $C_1$–$C_6$ alkoxyimino and the like. Suitable examples of the acyl groups represented by $R_3$ are 2-thienylacetyl, phenylacetyl, phenoxyacetyl, furylacetyl, pyridylacetyl, pyrimidylacetyl, oxazolylacetyl, oxadiazolylacetyl, thiazolylacetyl, thiadiazolylacetyl, triazolylacetyl, tetrazolylacetyl, 2-amino-thiazol-4-yl-acetyl, α-syn-methoxyimino-α-(2-amino-thiazol-4-yl)acetyl, {D(−)-α-(4-ethyl-2,3-dioxo-1-piperazinecarboxamide)-α-4-hydroxyphenyl}acetyl, {(Z)-2-(2-aminothiazol-4-yl)-2-(2-carboxypropyloxyimino)}-acetyl, formyl, acetyl, propionyl, tetrazolylthioacetyl, 4-pyridylthioacetyl, 4-pyridyloxyacetyl, benzoyl, p-nitrobenzoyl, 4-isoxazolylcarbonyl, etc.

The process of the invention is usually carried out as follows.

A penam derivative of the formula (II) is reacted with a heterocyclic compound of the formula H—N(Y)(III) in the presence or absence of a base to give a compound of the formula (I). The reaction is conducted in a suitable solvent by reacting the heterocyclic compound of the formula (III) with the known penam derivative of the formula (II) (U.S. Pat. No. 4,496,484) wherein the heterocyclic compound of the formula (III) is used in an amount of about 1 to 50 moles, preferably about 10 to about 30 moles, per mole of the penam derivative of the formula (II), or alternatively by reacting the compound of the formula (III) with the derivative of the formula (II) in the presence of a base or a metal salt in a solvent wherein the base or metal salt is used in an amount of about 0.5 to about 2 moles per mole of the derivative of the formula (II) and wherein the compound of the formula (III) is used in an amount of about 1 to about 10 moles per mole of the derivative of the formula (II). Examples of the base or metal salt include alkali metal carbonates such as sodium hydrogencarbonate, potassium hydrogencarbonate and cesium carbonate, alkaline earth metal carbonates such as barium carbonate and calcium carbonate, carbonates of the copper group metals such as silver carbonate and copper carbonate, oxides of the copper group metals such as copper oxide and silver oxide, alkaline earth metal oxides such as magnesium oxide, calcium oxide and barium oxide, oxides of the zinc group metals such as zinc oxide and mercury oxide, oxides of the aluminum group metals such as aluminum oxide and thallium oxide, oxides of the carbon group metals such as tin oxide and zinc oxide, oxides of the iron group metals such as iron oxide, cobalt oxide and nickel oxide, hydroxides of the copper group metals such as copper hydroxide and silver hydroxide, organic amines such as pyridine, triethylamine and diisopropylethylamine, and anion exchange resin.

The solvent to be used is not particularly limited insofar as it does not adversely affect the reaction and includes, for example, acetonitrile, acetone, methyl ethyl ketone, dimethylformamide, nitromethane, tetrahydrofuran, dioxane, methanol, ethanol, methoxyethanol, dichloromethane and the like. These organic solvents are usable singly or at least two of them can be used in mixture. The organic solvent can be also used as mixed with water. The reaction is conducted usually at about 0° to about 80° C., preferably about 20° to 50° C. Generally the reaction is completed within 1 to 20 hours, and in many cases within 1 to 5 hours. After completion of the reaction, the desired compound is separated and collected by conventional methods. When required, the contemplated compound of the formula (I) can be purified by recrystallization, thin layer chromatography, column chromatography or the like.

The compounds of the formula (I) prepared by the process of the present invention can be converted to compounds useful as antibiotics by changing the protecting group R by the usual method into a group capable of forming an ester to be easily hydrolyzed in vivo, or by conventional de-estrification of the protecting group R into a free-acid form, or by being made into a pharmaceutically acceptable salt by the conventional method.

Furthermore, the compounds of the formula (I) prepared by the process of the present invention are also useful as intermediates for synthesizing β-lactamase inhibitors. Examples of such β-lactamase inhibitors include compounds represented by the formula (V)

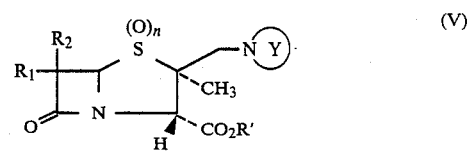

wherein n is 1 or 2, and $R_1$, $R_2$ and —N(Y) are as defined above and R' is hydrogen or has the same meaning as R in the formula (I), particularly a compound of the formula (V) wherein $R_1$ and $R_2$ are each hydrogen. The β-lactamase inhibitor of the formula (V) can be prepared from a compound of the formula (I), for example, by oxidizing the compound (I) to a monooxide compound of the formula (V) wherein n is 1, which can then be converted to a dioxide compound of the formula (V) wherein n is 2. The oxidation reaction employs common oxidizing agents such as permanganic acid, periodic acid, peracetic acid, trifluoroperacetic acid, perbenzoic acid and hydrogen peroxide. These oxidizing agents may be used optionally in excess, but may preferably be used in an amount of about 1 to about 5 moles per mole of the compound of the formula (I). The intermediate, i.e., monooxide of the formula (V) wherein n is 1, is prepared by suitably selecting the reaction conditions and the kind and amount of the oxidizing agent. The reaction is usually carried out in a suitable solvent.

Examples of the solvent can be any of those which does not affect the oxidation reaction such as dichloromethane, chloroform, carbon tetrachloride, pyridine, tetrahydrofuran, dioxane, acetone, formic acid, dimethylformamide, ethyl acetate and water. The reaction temperature is not particularly limited but generally about 0° to about 60° C.

The compound of the formula (V) thus obtained is subjected to the de-esterification reaction as contained in, or as isolated from, the reaction mixture obtained to give the penicillanic acid derivative of the formula (V) wherein R' is hydrogen.

The de-esterification method which can be employed includes various conventional methods such as reduction, hydrolysis and the like which permits the conversion of a protected carboxyl group to a carboxyl group. Especially when the penicillin carboxyl-protecting group represented by R is trichloroethyl, benzyl, diphenylmethyl, p-nitrobenzyl or the like, the de-esterification is advantageously conducted by reduction. When the protecting group is p-methoxybenzyl, tert-butyl, trityl, diphenylmethyl, methoxymethyl, tetrahydropyranyl, tert-butyldimethylsilyl or the like, the reaction is advantageously carried out using an acid.

Typical reduction can be effected by using a mixture of (a) a metal such as zinc or zinc-amalgam and/or a chromium salt such as chromium chloride or chromium acetate and (b) an acid such as formic acid or acetic acid, or can be catalytically performed. Examples of catalysts useful in the catalytic reduction are platinum, platinum oxide, palladium, palladium oxide, palladium-barium sulfate, palladium-calcium carbonate, palladium-carbon, nickel oxide, Raney-nickel and the like. Useful solvents are not particularly limited insofar as they do not adversely affect the reaction. Examples of preferable solvents includes alcohols such as methanol and ethanol, ethers such as tetrahydrofuran and dioxane, esters such as ethyl acetate, fatty acids such as acetic acid, and a mixture of these organic solvents with water.

Examples of acids which can be used to convert the carboxyl protecting group to carboxy group are lower fatty acids such as formic acid and acetic acid, trihaloacetic acids such as trichloroacetic acid and trifluoroacetic acid, hydrohalogenic acids such as hydrochloric acid and hydrofluoric acid, organic sulfonic acids such as p-toluenesulfonic acid or mixtures of these acids. When a liquid acid is used in the reaction involving the use of an acid, an additional solvent is not particularly required. However, it is possible to use a solvent which will not adversely affect the reaction, e.g., dimethylformamide, dichloromethane, chloroform, carbon tetrachloride, tetrahydrofuran, dioxane, acetone, etc.

The penicillin derivative of the formula (V) thus obtained in the form of free acid can be converted to the desired pharmaceutically acceptable salt or ester by the salt-forming and/or esterification reaction conventionally employed in the art.

When the monooxide or the dioxide of the formula (V) prepared in this way is used conjointly with a known β-lactam antibiotic selected from a wide variety of conventional ones, the antibacterial activity of the β-lactam antibiotic is increased. The ratio of the compound of the formula (V) to the β-lactam antibiotic is 1:0.1 to 10, preferably 1:0.2 to 5, by weight.

Given below are examples to illustrate the invention in detail.

EXAMPLE 1

Preparation of p-nitrobenzyl 2α-methyl-2β-(1,2,3-triazol-2-yl)methylpenam-3α-carboxylate and p-nitrobenzyl 2α-methyl-2β-(1,2,3-triazol-1-yl)methylpenam-3α-carboxylate A 741 mg quantity of p-nitrobenzyl 2β-chloromethyl-2α-methylpenam-3α-carboxylate, 276 mg of 1,2,3-triazole and 185 mg of sodium hydrogencarbonate were reacted in a mixture of 6 ml of acetone and 1.5 ml of water at 40° C. for 12 hours with heating and stirring. The acetone was distilled away under reduced pressure, and the residue was extracted with 15 ml of methylene chloride. The methylene chloride was then distilled away, and the resulting residue was purified by silica gel column chromatography (eluent:chloroform-acetone=19:1), giving as a first eluate 186 mg of p-nitrobenzyl 2α-methyl-2β-(1,2,3-triazol-2-yl)methylpenam-3α-carboxylate.

M.p.: 160°–161° C.

Infrared absorption spectrum (KBr) $\nu_{C=O}$ (cm$^{-1}$)=1784, 1758

Nuclear magnetic resonance spectrum (CDCl$_3$)

δ (ppm)=1.25 (3H, s), 3.19 and 3.64 (each 1H, AB-X), 4.69 (2H, s), 5.25 (2H, AB), 5.34–5.41 (1H, m), 5.58 (1H, s), 7.67 (2H, s), 7.51 and 8.23 (each 2H, each d)

Produced as a second eluate was 186 mg of p-nitrobenzyl 2α-methyl-2β-(1,2,3-triazol-1-yl)methylpenam-3α-carboxylate.

M.p.: 111°–112° C.

Infrared absorption spectrum (KBr)

$\nu_{C=O}$ (cm$^{-1}$)=1776, 1745

Nuclear magnetic resonance spectrum (CDCl$_3$)

δ (ppm)=1.41 (3H, s), 3.21 and 3.70 (each 1H, AB-X), 4.61 (2H, s), 4.88 (1H, s), 5.26 (2H, s), 5.39–5.46 (1H, m), 7.75 (1H, d), 7.78 (1H, d), 7.51 and 8.24 (each 2H, each d)

EXAMPLE 2

Preparation of p-nitrobenzyl 2α-methyl-2β-(1,2,3-triazol-yl)methylpenam-3α-carboxylate A 400 mg quantity of p-nitrobenzyl 2β-chloromethyl-2α-methylpenam-3α-carboxylate, 1.117 g of 1,2,3-triazole and 297 mg of silver carbonate were heated with stirring in a mixture of 2.1 ml of acetone and 0.7 ml of water at 40° C. for 3 hours. After cooling, the insolubles were removed by filtration and the filtrate was extracted with 15 ml of methylene chloride. The methylene chloride was distilled off and the residue was subjected to silica gel column chromatography (eluent:chloroformacetone=19:1), giving 339 mg of p-nitrobenzyl 2α-methyl-2β-(1,2,3-triazol-1-yl)methylpenam-3α-carboxylate.

The compound thus obtained was identical in the melting point, infrared absorption spectrum (KBr) and nuclear magnetic resonance spectrum (CDCl$_3$) with the second eluate prepared in Example 1.

EXAMPLE 3

Preparation of p-nitrobenzyl 2α-methyl-2β-(1,2,3-triazol-2-yl)methylpenam-3α-carboxylate and p-nitrobenzyl 2α-methyl-2β-(1,2,3-triazol-1-yl)methylpenam-3α-carboxylate A 185 mg quantity of p-nitrobenzyl 2β-chloromethyl-2α-methylpenam-3α-carboxylate and 689 mg of 1,2,3-triazole were stirred with heating in a mixture of 3.75 ml of acetonitrile and 1.25 ml of water at 30° C. for 6 hours. The acetonitrile was distilled off under reduced pressure and the residue was extracted with 15 ml of methylene chloride. The methylene chloride was distilled off and the residue was subjected to silica gel column chromatography (eluent:chloroform-acetone=19:1), giving 37 mg of p-nitrobenzyl 2α-methyl-2β-(1,2,3-triazol-2-yl)methylpenam-3α-carboxylate as a first eluate. Produced as a second eluate was 140 mg of p-nitrobenzyl 2α-methyl-2β-(1,2,3-triazol-1-yl)methylpenam-3α-carboxylate.

The compounds thus obtained were each identical in the melting point, infrared absorption spectrum (KBr) and nuclear magnetic resonance spectrum (CDCl$_3$) with the respective first and second eluates prepared in Example 1.

EXAMPLE 4

Preparation of p-nitrobenzyl 2α-methyl-2β-(1,2,3-triazol-1-yl)methylpenam-3α-carboxylate A 400 mg quantity of p-nitrobenzyl 2β-chloromethyl-2α-methylpenam-3α-carboxylate, 1.117 g of 1,2,3-triazole and 1 ml of anion exchange resin (product of Mitsubishi Chemical Corporation, Japan, tradename "Diaion WA 30") were heated with stirring in a mixture of 2.1 ml of acetone and 0.7 ml of water at 40° C. for 3 hours. After cooling, the resin was filtered and the filtrate was extracted with 15 ml of methylene chloride. The methylene chloride was distilled off and the residue was subjected to silica gel column chromatography (eluent:chloroform-acetone=19:1), giving 326 mg of p-nitrobenzyl 2α-methyl-2β-(1,2,3-triazol-1-yl)methylpenam-3α-carboxylate.

The compound thus obtained was identical in the melting point, infrared absorption spectrum (KBr) and nuclear magnetic resonance spectrum (CDCl$_3$) with the second eluate prepared in Example 1.

EXAMPLE 5

Preparation of p-nitrobenzyl-2α-methyl-2β-(tetrazol-1-yl)methylpenam-3α-carboxylate and p-nitrobenzyl 2α-methyl-2β-(tetrazol-2-yl)methylpenam-3α-carboxylate A mixture of 185 mg of p-nitrobenzyl 2β-chloromethyl-2α-methylpenam-3α-carboxylate, 50 mg of potassium hydrogencarbonate and 105 mg of tetrazole was stirred at 30° C. for 12 hours in a mixture of 3.75 ml of acetone and 1.25 ml of water. The reaction mixture was concentrated under reduced pressure and the concentrate was extracted with ethyl acetate. The extract was washed with an aqueous solution of sodium chloride, and dried over magnesium sulfate. The solvent was then distilled away under reduced pressure. The residue was subjected to silica gel column chromatography (eluent:-benzene-ethyl acetate=19:1) to give 71 mg of p-nitrobenzyl 2α-methyl-2β-(tetrazol-2-yl)methylpenam-3α-carboxylate as a first elutate.

Infrared absorption spectrum (CHCl$_3$)
$\nu_{C=O}$ (cm$^{-1}$)=1780, 1750

Nuclear magnetic resonance spectrum (CDCl$_3$)
δ (ppm)=1.29 (3H, s), 3.15 (1H, AB-X, J=2, 16 Hz), 3.67 (1H, AB-X, J=4, 16 Hz), 4.87 (2H, s), 5.23 (2H, s), 5.36 (1H, s), 5.30–5.45 (1H, m), 7.46 (2H, d), 8.16 (2H, d), 8.53 (1H, s)

A 66 mg quantity of p-nitrobenzyl 2α-methyl-2β-(tetrazol-1-yl)methylpenam-3α-carboxylate was subsequently obtained as a second eluate.

Infrared absorption spectrum (CHCl$_3$)
$\nu_{C=O}$ (cm$^{-1}$)=1770, 1745

Nuclear magnetic resonance spectrum (CDCl$_3$)
δ (ppm)=1.41 (3H, s), 3.17 (1H, AB-X, J=2, 16 Hz), 3.69 (1H, AB-X, J=4, 16 Hz), 4.67 (2H, s), 4.84 (1H, s), 5.24 (2H, s), 5.38 (1H, AB-X, J=2, 4 Hz), 7.43 (2H, d), 8.13 (2H, d), 8.82 (1H, s)

EXAMPLE 6

Preparation of p-nitrobenzyl 2β-(imidazol-1-yl)methyl-2α-methylpenam-3α-carboxylate A 185 mg quantity of p-nitrobenzyl 2β-chloromethyl-2α-methylpenam-3α-carboxylate, 138 mg of silver carbonate and 68 mg of imidazole were heated at 30° C. for 5 hours in a mixture of 1.5 ml of acetonitrile and 0.5 ml of water with stirring. The reaction mixture was filtered on a Celite pad while being washed with ethyl acetate. The filtrate was washed with water and an aqueous solution of sodium chloride, and dried over magnesium sulfate. The solvent was distilled off under reduced pressure. The residue was purified by silica gel column chromatography (eluent:chloroform-acetone=19:1), giving 68 mg of p-nitrobenzyl 2β-(imidazol-1-yl)methyl-2α-methylpenam-3α-carboxylate.

Infrared absorption spectrum (CHCl$_3$)
$\nu_{C=O}$ (cm$^{-1}$)=1773, 1750

Nuclear magnetic resonance spectrum (CDCl$_3$)
δ (ppm)=1.37 (3H, s), 3.13 (1H, AB-X, J=2, 16 Hz), 3.69 (1H, AB-X, J=4, 16 Hz), 4.16 (2H, s), 4.69 (1H, s), 5.22 (2H, s), 5.36 (1H, AB-X, J=2, 4 Hz), 7.01 (2H, s), 7.45 (2H, d), 7.51 (1H, s), 8.16 (2H, d)

EXAMPLE 7

Preparation of p-nitrobenzyl 2α-methyl-2β-(1,2,4-triazol-1-yl)methylpenam-3α-carboxylate Following the general procedure of Example 6, 185 mg of p-nitrobenzyl 2β-chloromethyl-2α-methylpenam-3α-carboxylate was reacted with 70 mg of 1,2,4-triazole, giving 60 mg of p-nitrobenzyl 2α-methyl-2β-(1,2,4-triazol-1-yl)methylpenam-3α-carboxylate.

Infrared absorption spectrum (CHCl$_3$)
$\nu_{C=O}$ (cm$^{-1}$)1770, 1745

Nuclear magnetic resonance spectrum (CDCl$_3$)
δ (ppm)=1.39 (3H, s), 3.15 (1H, J=2, 16 Hz), 3.70 (1H, AB-X, J=4, 16 Hz), 4.39 (2H, s), 5.14 (1H, s), 5.26 (2H, s), 5.43 (1H, AB-X, J=2, 4 Hz), 7.49 (2H, d), 7.96 (1H, s), 8.17 (1H, s), 8.20 (2H, d)

EXAMPLE 8

Preparation of p-nitrobenzyl 2β-(benzotriazol-1-yl)methyl-2α-methylpenam-3α-carboxylate Following the general procedure of Example 6, 185 mg of p-nitrobenzyl 2β-chloromethyl-2α-methylpenam-3α-carboxylate was reacted with 119 mg of benzotriazole to give 77 mg of p-nitrobenzyl 2β-(benzotriazol-1-yl)methyl-2α-methylpenam-3α-carboxylate.

Infrared absorption spectrum (CHCl$_3$)
$\nu_{C=O}$ (cm$^{-1}$)=1775, 1750

Nuclear magnetic resonance spectrum (CDCl$_3$)
δ (ppm)=1.43 (3H, s), 3.14 (1H, AB-X, J=2, 16 Hz), 3.68 (1H, AB-X, J=4, 16 Hz), 4.86 (2H, s), 5.20 (3H, s), 5.37 (1H, AB-X, J=2, 4 Hz), 7.30–8.30 (8H, m)

EXAMPLE 9

Preparation of p-nitrobenzyl 2α-methyl-2β-(1,2,4-triazol-1-yl)methylpenam-3α-carboxylate A 370 mg quantity of p-nitrobenzyl 2β-chloromethyl-2α-methylpenam-3α-carboxylate and 1.38 g of 1,2,4-triazole were reacted with stirring at 30° C. for 5 hours in a mixture of 3 ml of acetonitrile and 1 ml of water. The reaction mixture was diluted with ethyl acetate and filtered. The filtrate was washed with an aqueous sodium bicarbonate solution and an aqueous sodium chloride solution, and dried over magnesium sulfate. The solvent was distilled off under reduced pressure. The residue was purified by silica gel column chromatography (eluent:chloroform-acetone=19:1) to give 166 mg of p-nitrobenzyl 2α-methyl-262 -(1,2,4-triazol-1-yl)methylpenam-3α-carboxylate.

The infrared absorption spectrum and nuclear magnetic resonance spectrum of this compound were identical with those of the compound obtained in Example 7.

EXAMPLE 10

Preparation of p-nitrobenzyl 2α-methyl-2β-(pyrazol-1-yl)methylpenam-3α-carboxylate A 1.111 g quantity of p-nitrobenzyl 2β-chloromethyl-2α-methylpenam-3α-carboxylate, 3.06 g of pyrazole and 833 mg of anion-exchange resin (Diaion WA30, product of Mitsubishi Chemical Corporation, Japan) were heated with stirring at 40° C. for one hour in a mixture of 9 ml of acetonitrile and 3 ml of water. The anion-exchange resin was filtered off, and the filtrate was separated after shaking with methylene chloride and water. The methylene chloride layer separated was dried over magnesium sulfate and the methylene chloride was distilled off under reduced pressure. The resulting residue was subjected to silica gel column chromatography (eluent:chloroform-acetone=19:1), giving 405 mg of p-nitrobenzyl 2α-methyl-2β-(pyrazol-1-yl)methylpenam-3α-carboxylate.

Infrared absorption spectrum (KBr)
$\nu_{C=O}$ (cm$^{-1}$)=1780, 1742

Nuclear magnetic resonance spectrum (CDCl$_3$)
δ (ppm)=1.35 (3H, s), 3.17 (1H, AB-X, J=2, 16 Hz), 3.64 (1H, AB-X, J=4, 16 Hz), 4.35 (2H, s), 5.26 (2H, s), 5.29 (1H, s), 5.35–5.41 (1H, m), 6.26–6.30 (1H, m), 7.46–7.56 (4H, m), 8.21 (2H, d)

EXAMPLE 11

Preparation of p-nitrobenzyl 2β-(4-methoxycarbonyl-5-methyl-1,2,3-triazol-2-yl)methyl-2α-methylpenam-3α-carboxylate, p-nitrobenzyl 2β-(5-methoxycarbonyl-4-methyl-1,2,3-triazol-1-yl)methyl-2α-methylpenam-3α-carboxylate and p-nitrobenzyl 2β-(4-methoxycarbonyl-5-methyl-1,2,3-triazol-1-yl)methyl-2α-methylpenam-3α-carboxylate A 185 mg quantity of p-nitrobenzyl 2β-chloromethyl-2α-methylpenam-3α-carboxylate, 213 mg of 4-methoxycarbonyl-5-methyl-1,2,3-triazole and 50 mg of potassium hydrogencarbonate were added to 2 ml of a mixture of acetonitrile and water (3:1), and the mixture was stirred at 40° C. for three hours. The reaction mixture was diluted with 15 ml of ethyl acetate, and washed twice respectively with an aqueous solution of sodium hydrogencarbonate and a saturated aqueous solution of sodium chloride. The mixture was dried over anhydrous magnesium sulfate and filtered. The filtrate was condensed under reduced pressure. The residue thus obtained was purified by silica gel column chromatography (eluent:benzene-ethyl acetate=19:1) to obtain 79 mg of p-nitrobenzyl 2β-(4-methoxycarbonyl-5-methyl-1,2,3-triazol-2-yl)methyl-2α-methylpenam-3α-carboxylate as a first eluate.

Infrared absorption spectrum (CHCl$_3$)
$\nu_{C=O}$ (cm$^{-1}$)=1773, 1740, 1720

Nuclear magnetic resonance spectrum (CDCl$_3$)
δ (ppm)=1.27 (3H, s), 2.46 (3H, s), 3.08 (1H, AB-X, J=2, 16 Hz), 3.61 (1H, AB-X, J=4, 16 Hz), 3.89 (3H, s), 4.60 (2H, s), 5.20 (2H, s), 5.29 (1H, AB-X, J=2, 4 Hz), 5.46 (1H, s), 7.41 (2H, d), 8.13 (2H, d)

Produced as a second eluate was 81 mg of p-nitrobenzyl 2β-(5-methoxycarbonyl-4-methyl-1,2,3-triazol-1-yl)methyl-2α-methylpenam-3α-carboxylate.

Infrared absorption spectrum (CHCl$_3$)
$\nu_{C=O}$ (cm$^{-1}$)=1775, 1742, 1723

Nuclear magnetic resonance spectrum (CDCl$_3$)
δ (ppm)=1.32 (3H, s), 2.51 (3H, s), 3.08 (1H, AB-X, J=2, 16Hz), 3.56 (1H, AB-X, J=4, 16 Hz), 3.91 (3H,s), 4.99 and 5.09 (2H, AB, J=14 Hz), 5.23 (2H, s), 5.15–5.35 (2H, m), 7.48 (2H, d), 8.16 (2H, d)

Produced as a third eluate was 41 mg of p-nitrobenzyl 2β-(4-methoxycarbonyl-5-methyl-1,2,3-triazol-1-yl)methyl-2α-methylpenam-3α-carboxylate.

Infrared absorption spectrum (CHCl$_3$)
$\nu_{C=O}$ (cm$^{-1}$)=1775, 1750, 1720

Nuclear magnetic resonance spectrum (CDCl$_3$)
δ (ppm)=1.40 (3H, s), 2.60 (3H,s), 3.08 (1H, AB-X, J=2, 16 Hz), 3.67 (1H, AB-X, J=4, 16 Hz), 3.93 (3H, s), 4.49 and 4.57 (2H, AB, J=14 Hz), 5.25 (2H, s), 5.20–5.45 (2H, m), 7.48 (2H, d), 8.18 (2H, d)

EXAMPLE 12

Preparation of pinitrobenzyl 2β-(4-methoxycarbonyl-1,2,3-triazol-2-yl)methyl-2α-methylpenam-3α-carboxylate, p-nitrobenzyl 2β-(5-methoxycarbonyl-1,2,3-triazol-1-yl)methyl-2α-methylpenam-3α-carboxylate and p-nitrobenzyl 2β-(4-methoxycarbonyl-1,2,3-triazol-1-yl)methyl-2α-methylpenam-3α-carboxylate A 185 mg quantity of p-nitrobenzyl 2β-chloromethyl-2α-methylpenam-3α-carboxylate, 190 mg of 4-methoxycarbonyl-1,2,3-triazole and 50 mg of potassium hydrogencarbonate were added to 5 ml of a mixture of acetone and water (3:1), and the mixture was stirred at 30° C. for three hours. The reaction mixture was diluted with 15 ml of ethyl acetate, and washed twice respectively with an aqueous solution of sodium hydrogencarbonate and a saturated aqueous solution of sodium chloride. The mixture was dried over anhydrous magnesium sulfate and filtered. The filtrate was condensed under reduced pressure. The residue thus obtained was purified by silica gel column chromatography (eluent:benzene-ethyl acetate=19:1) to obtain 81 mg of p-nitrobenzyl 2β-(4-methoxycarbonyl-1,2,3-triazol-2-yl)methyl-2α-methylpenam-3α-carboxylate as a first eluate.

Infrared absorption spectrum (CHCl$_3$)
$\nu_{C=O}$ (cm$^{-1}$)=1780, 1740

Nuclear magnetic resonance spectrum (CDCl$_3$)
δ (ppm)=1.28 (3H, s), 3.11 (1H, AB-X, J=2, 16 Hz), 3.46 (1H, AB-X, J=4, 16 Hz), 3.93 (3H, s), 4.73 (2H, s), 5.24 (2H, s), 5.36 (1H, AB-X, J=2, 4 Hz), 5.47 (1H, s), 7.49 (2H, d), 8.09 (1H, s), 8.20 (2H, d)

Produced as a second eluate was 44 mg of p-nitrobenzyl 2β-(5-methoxycarbonyl-1,2,3-triazol-1-yl)methyl-2α-methylpenam-3α-carboxylate.

Infrared absorption spectrum (CHCl$_3$)
$\nu_{C=O}$ (cm$^{-1}$)=1780, 1740

Nuclear magnetic resonance spectrum (CDCl$_3$)
δ (ppm)=1.33 (3H, s), 3.11 (1H, AB-X, J=2, 16 Hz), 3.60 (1H, AB-X, J=4, 16 Hz), 3.91 (3H, s), 4.98 and 5.20 (2H, AB, J=14 Hz), 5.25 (2H, s), 5.20–5.40 (2H, m), 7.49 (2H, d), 8.09 (1H, s), 8.19 (2H, d)

Produced as a third eluate was 63 mg of p-nitrobenzyl 2β-(4-methoxycarbonyl-1,2,3-triazol-1-yl)methylpenam-3α-carboxylate.

Infrared absorption spectrum (CHCl$_3$)
$\nu_{C=O}$ (cm$^{-1}$)=1780, 1740

Nuclear magnetic resonance spectrum (CDCl$_3$)
δ (ppm)=1.40 (3H, s), 3.17 (1H, AB-X, J=2, 16 Hz), 3.70 (1H, AB-X, J=4, 16 Hz), 3.93 (3H, s), 4.66 (2H, s), 4.91 (1H, s), 5.25 (2H, s), 5.40 (1H, AB-X, J=2, 4 Hz), 7.49 (2H, d), 8.19 (2H, d), 8.30 (1H, s)

EXAMPLE 13

Preparation of p-nitrobenzyl 2β-(4,5-dimethoxycarbonyl-1,2,3-triazol-2-yl)methyl-2α-methylpenam-3α-carboxylate and p-nitrobenzyl 2β-(4,5-dimethoxycarbonyl-1,2,3-triazol-1-yl)methyl-2α-methylpenam-3α-carboxylate A 185 mg quantity of p-nitrobenzyl 2β-chloromethyl-2α-methylpenam-3α-carboxylate, 278 mg of 4,5-dimethoxycarbonyl-1,2,3-triazole and 50 mg of potassium hydrogencarbonate were added to 5 ml of a mixture of acetone and water (3:1), and the mixture was stirred at 30° C. for 16 hours. The reaction mixture was diluted with 15 ml of ethyl acetate, and washed twice respectively with an aqueous solution of sodium hydrogencarbonate and a saturated aqueous solution of sodium chloride. The mixture was dried over anhydrous magnesium sulfate and filtered. The filtrate was condensed under reduced pressure. The residue thus obtained was purified by silica gel column chromatography (eluent:benzene-ethyl acetate=19:1), giving 99 mg of p-nitrobenzyl 2β-(4,5-dimethoxycarbonyl-1,2,3-triazol-2-yl)methyl-2α-methylpenam-3α-carboxylate as a first eluate.

Infrared absorption spectrum (CHCl$_3$)
$\nu_{C=O}$ (cm$^{-1}$)=1780, 1747
Nuclear magnetic resonance spectrum (CDCl$_3$)
δ (ppm)=1.33 (3H, s), 3.12 (1H, AB-X, J=2, 16 Hz), 3.68 (1H, AB-X, J=4, 16 Hz), 3.93 (6H, s), 4.74 (2H, s), 5.22 (2H, s), 5.15–5.40 (1H, m), 5.37 (1H, s), 7.46 (2H, d), 8.14 (2H, d)

Produced as a second eluate was 90 mg of p-nitrobenzyl 2β-(4,5-dimethoxycarbonyl-1,2,3-triazol-1-yl)methyl-2α-methylpenam-3α-carboxylate.

Infrared absorption spectrum (CHCl$_3$)
$\nu_{C=O}$ (cm$^{-1}$)=1780, 1750 (sh), 1735
Nuclear magnetic resonance spectrum (CDCl$_3$)
δ (ppm)=1.34 (3H, s), 3.09 (1H, AB-X, J=2, 16 Hz), 3.57 (1H, AB-X, J=4, 16 Hz), 3.90 (6H, s), 4.88 (2H, s), 5.11 (1H, s), 5.20 (2H, s), 5.15–5.35 (1H, m), 7.43 (2H, d), 8.10 (2H, d)

EXAMPLE 14

Preparation of p-nitrobenzyl 2β-(4-p-nitrobenzyloxycarbonyl-1,2,3-triazol-2-yl)methyl-2α-methylpenam-3α-carboxylate, p-nitrobenzyl 2β-(5-p-nitrobenzyloxycarbonyl-1,2,3-triazol-1-yl)methyl-2α-methylpenam-3α-carboxylate, and p-nitrobenzyl 2β-(4-p-nitrobenzyloxycarbonyl-1,2,3-triazol-1-yl)methyl-2α-methylpenam-3α-carboxylate Following the general procedure of Example 12 and using appropriate starting materials, 130 mg of p-nitrobenzyl 2β-(4-p-nitrobenzyloxycarbonyl-1,2,3-triazol-2-yl)methyl-2α-methylpenam-3α-carboxylate was obtained as a first eluate.

Infrared absorption spectrum (CHCl$_3$)
$\nu_{C=O}$ (cm$^{-1}$)=1780, 1740
Nuclear magnetic resonance spectrum (CDCl$_3$)
δ (ppm)=1.32 (3H, s), 3.12 (1H, AB-X, J=2, 16 Hz), 3.66 (1H, AB-X, J=4, 16 Hz), 4.65 (2H, s), 5.22 (2H, s), 5.15–5.50 (2H, m), 5.45 (2H, s), 7.30–8.30 (9H, m)

Produced as a second eluate was 50 mg of p-nitrobenzyl 2β-(5-p-nitrobenzyloxycarbonyl-1,2,3-triazol-1-yl)methyl-2α-methylpenam-3α-carboxylate.

Infrared absorption spectrum (CHCl$_3$)
$\nu_{C=O}$ (cm$^{-1}$)=1780, 1740
Nuclear magnetic resonance spectrum (CDCl$_3$)
δ (ppm)=1.36 (3H, s), 3.03 (1H, AB-X, J=2, 16 Hz), 3.55 (1H, AB-X, J=4, 16 Hz), 5.00 and 5.10 (2H, AB, J=14 Hz), 5.21 (2H, s), 5.15–5.45 (2H, m), 5.39 (2H, s), 7.30–8.30 (9H, m)

Produced as a third eluate was 75 mg of p-nitrobenzyl 2β-(4-p-nitrobenzyloxycarbonyl-1,2,3-triazol-1-yl)methyl-2α-methylpenam-3α-carboxylate.

Infrared absorption spectrum (CHCl$_3$)
$\nu_{C=O}$ (cm$^{-1}$)=1780, 1750
Nuclear magnetic resonance spectrum (CDCl$_3$)
δ (ppm)=1.40 (3H, s), 3.11 (1H, AB-X, J=2, 16 Hz), 3.63 (1H, AB-X, J=4, 16 Hz), 4.63 (2H, s), 4.84 (1H, s), 5.10 (2H, m), 5.40 (2H, s), 7.20–8.35 (9H, m)

EXAMPLE 15

Preparation of p-nitrobenzyl 2β-(4-phenyl-1,2,3-triazol-2-yl)methyl-2α-methylpenam-3α-carboxylate Following the general procedure of Example 11 and using appropriate starting materials, 75 mg of 2β-(4-phenyl-1,2,3-triazol-2-yl)methy-2α-methylpenam-3α-carboxylate was prepared.

Infrared absorption spectrum (CHCl$_3$)
$\nu_{C=O}$ (cm$^{-1}$)=1780, 1750 (sh)
Nuclear magnetic resonance spectrum (CDCl$_3$)
δ (ppm)=1.30 (3H, s), 3.14 (1H, AB-X, J=2, 16 Hz), 3.65 (1H, AB-X, J=4, 16 Hz), 4.65 (2H, s), 5.15 (2H, s), 5.34 (1H, AB-x, J=2, 4 Hz), 5.65 (1H, s), 7.15–7.90 (7H, m), 7.91 (1H, s), 8.13 (2H, d)

EXAMPLE 16

Preparation of p-nitrobenzyl 2β-(4-formyl-1,2,3-triazol-2-yl)methyl-2α-methylpenam-3α-carboxylate Following the general procedure of Example 11 and using appropriate starting materials, a 76 mg quantity of p-nitrobenzyl 2β-(4-formyl-1,2,3-triazol-2-yl)methyl-2α-methylpenam-3α-carboxylate was prepared.

Infrared absorption spectrum (CHCl$_3$)
$\nu_{C=O}$ (cm$^{-1}$)=1780, 1750, 1700
Nuclear magnetic resonance spectrum (CDCl$_3$)
δ (ppm)=1.30 (3H, s), 3.12 (1H, AB-X, J=2, 16 Hz), 3.76 (1H, AB-X, J=4, 16 Hz), 4.72 (2H, s), 5.22 (2H, s), 5.33 (1H, AB-X, J=2, 4 Hz), 5.45 (1H, s), 7.43 (2H, d), 8.03 (1H, s), 8.15 (2H, d), 10.00 (1H, s)

EXAMPLE 17

Preparation of p-methoxybenzyl 6α-bromo-2α-methyl-2β-(1,2,3-triazol-1-yl)methylpenam-3α-carboxylate A 238 mg quantity of p-methoxybenzyl 6α-bromo-2β-chloromethyl-2α-methylpenam-3α-carboxylate, 755 mg of 1,2,3-triazole and 80 mg of silver carbonate were heated in a mixture of 2.25 ml of actonitrile and 0.75 ml of water with stirring at 60° C. for 2 hours. After cooling, the insolubles were filtered off, and the filtrate was extracted with 15 ml of methylene chloride. Then the methylene chloride was distilled off. The residue obtained was subjected to silica gel column chromatography (eluent:chloroform-acetone=19:1), giving 141 mg of p-methoxybenzyl 6α-bromo-2α-methyl-2β-(1,2,3-triazol-1-yl)methylpenam-3α-carboxylate.

Infrared absorption spectrum (KBr)
$\nu_{C=O}$ (cm$^{-1}$)=1785, 1730
Nuclear magnetic resonance spectrum (CDCl$_3$)
δ (ppm)=1.33 (3H, s), 3.81 (3H, s), 4.50 (2H, s), 4.85 (1H, s), 4.88 (1H, d, J=1.4 Hz), 5.11 (2H, s), 5.49 (1H, d, J=1.4 Hz), 6.87 (2H, d, J=8.6 Hz), 7.27 (2H, d, J=8.6 Hz), 7.72 (2H, s)

EXAMPLE 18

Preparation of p-methoxybenzyl 6,6-dibromo-2α-methyl-2β-(1,2,3-triazol-1-yl)methylpenam-3α-carboxylate A 189 mg quantity of p-methoxybenzyl 6,6-dibromo-2β-chloromethyl-2α-methyl-3α-carboxylate, 765 mg of 1,2,3-triazole and 54 mg of silver carbonate were heated in a mixture of 2.25 ml of acetonitrile and 0.75 ml of water with stirring at 50° C. for 7 hours. After cooling, the same procedure as described in Example 17 was repeated, giving 84 mg of p-methoxybenzyl 6,6-dibromo-2α-methyl-2β-(1,2,3-triazol-1-yl)methylpenam-3α-carboxylate.

Infrared absorption spectrum (Neat)
$\nu_{C=O}$ (cm$^{-1}$)=1800, 1740
Nuclear magnetic resonance spectrum (CDCl$_3$)
δ (ppm)=1.27 (3H, s), 3.77 (3H, s), 4.34 and 4.67 (each 1H, AB, J=15 Hz), 4.83 (1H, s), 5.10 (2H, s), 5.83 (1H, s), 6.80 (2H, d, J=8.5 Hz), 7.29 (2H, d, J=8.5 Hz), 7.65 (1H, d, J=1.6 Hz), 7.78 (1H, d, J=1.6 Hz)

EXAMPLE 19

Preparation of tirchloroethyl 2α-methyl-6βδ-phenylacetylamino-2β-(1,2,3-triazol-1-yl)methylpenam-3α-carboxylate A 500 mg quantity of trichloroethyl 2β-chloromethyl-2α-methyl-6β-phenylacetylaminopenam-3α-carboxylate, 1.38 g of 1,2,3-triazole and 280 mg of anion exchange resin (product of Mitsubishi Chemical Corporation, Japan, trade name "Diaion WA-30") were heated in a mixture of 3 ml of acetonitrile and 1 ml of water with stirring at 40° C. for 3 hours. After cooling, the general procedure of Example 17 was followed, giving 240 mg of trichloroethyl 2α-methyl-6β-phenylacetylamino-2β-(1,2,3-triazol-1-yl)-methylpenam-3α-carboxylate.

EXAMPLE 20

Preparation of p-nitrobenzyl 2α-methyl-6β-phenoxyacetylamino-2β-(1,2,3-triazol-1-yl)methylpenam-3α-carboxylate Following the general procedure of Example 19 and using 520 mg of p-nitrobenzyl 2β-chloromethyl-2α-methyl-6β-phenoxyacetylaminopenam-3α-carboxylate, 1.38 g of 1,2,3-triazole and 280 mg of anion exchange resin (product of Mitsubishi Chemical Corporation, Japan, trade name "Diaion WA-30"), 232 mg of p-nitrobenzyl 2α-methyl-6β-phenoxyacetylamino-2β-(1,2,3-triazol-1-yl)methylpenam-3α-carboxylate was obtained.

The process of the present invention can be used to produce compounds disclosed in an application filed of even date herewith by the present applicants, and entitled "2β-Substituted-Methylpencillanic Acid Derivatives, and Salts and Esters Thereof" U.S. Ser. No. 123,631, the disclosure of which is hereby incorporated by reference for the teachings of such compounds, and the methods of use and utility thereof, therein.

We claim:

1. A process for preparing a 2β-substituted-methylpenicillin derivative represented by the formula

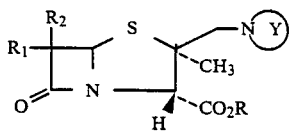
(I)

wherein R is hydrogen or a carboxyl protecting group, $R_1$ is hydrogen or halogen, $R_2$ is hydrogen, lower alkyl, lower alkoxy, halogen, azido, lower alkylthio, pthalimide or a group —NHR$_3$, wherein $R_3$ is hydrogen or acyl, and —N Y is an optionally substituted monocyclic or bicyclic heterocyclic group having 1 to 4 nitrogen atoms as hereto atom in the ring structure, the process comprising reacting a compound represented by the formula

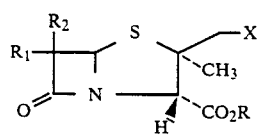
(II)

wherein X is chlorine or bromine, and R, $R_1$ and $R_2$ are as defined above with heterocyclic compound represented by the formula

(III)

wherein —N Y is as defined above, wherein the reaction is carried out in a solvent at a temperature of about 0° to about 80° C. and the heterocyclic compound of formula III is used in amounts of about 1 to about 50 moles per mole of the penam derivative of formula II.

2. A process as defined in claim 1 wherein —N Y is a 5-membered monocyclic heterocyclic ring group having 1 to 4 nitrogen atoms in its ring structure or a bicyclic heterocyclic ring group wherein a 5-membered heterocyclic group containing 2 or 3 nitrogen atoms in its ring structure is fused with a benzene ring or a bicyclic heterocyclic ring group wherein a 5-membered heterocyclic ring group containing 1 or 2 nitrogen atoms in its ring structure is fused with a 6-membered heterocyclic ring containing 1 or 2 nitrogen atoms in its ring structure, and said monocyclic heterocyclic ring group and said bicyclic heterocyclic ring group may optionally have 1-3 substituents, said substituents being selected from the group consisting of alkyl, alkoxy, hydroxyl, halogen, nitro, amino, alkoxycarbonyl, formyl, benzyloxycarbonyl, aryl and aralkyl; said benzyloxycarbonyl optionally having 1 to 3 substituents selected from the group consisting of $C_1$–$C_6$ alkyl, nitro and halogen atom on the benzene ring and said aryl optionally being substituted with 1 to 3 $C_1$–$C_6$ alkyl groups on the benzene ring.

3. A process as defined in claim 1 wherein —N Y is pyrrolyl, imidazolyl, pyrazolyl, tetrazolyl, 1,2,3-triazolyl, 1,2,4-triazolyl, benzotriazolyl, benzimidazolyl or purinyl, each of which may optionally be substituted with 1 to 3 substituents selected from the group consisting of $C_1$–$C_6$ alkyl, $C_1$–$C_6$ alkoxy, hydroxyl, halogen atom, nitro, amino, formyl, $C_2$–$C_7$ alkoxycarbonyl, benzyloxycarbonyl optionally having 1 to 3 substituents selected from the group consisting of $C_1$–$C_6$ alkyl, nitro and halogen atom on the benzene ring, phenyl optionally having 1 to 3 $C_1$–$C_6$ alkyl groups on the benzene ring and $C_1$–$C_6$ alkyl substituted with 1 to 3 phenyl groups.

4. A process as defined in claim 1 wherein the carboxyl protecting group is substituted or unsubstituted alkyl group, substituted or unsubstituted aralkyl group, acyloxyalkyl group, alkoxyalkyl group, lactone group, substituted or unsubstituted phenyl group, (5-substituted or unsubstituted-2-oxo-1,3-dioxoden-4-yl)methyl group, tetrahydropyranyl group, dimethylaminoethyl group, dimethylchlorosilyl group, trichlorosilyl group or tertbutyldimethylsilyl group.

5. A process as defined in claim 1 wherein acyl group represented by $R_3$ is one formed by removing a hydroxyl group from the carboxyl group of a fatty acid having 1 to 6 carbon atoms; one formed by removing a hydroxy group from the carboxyl group of an aromatic or heterocyclic carboxylic group wherein an aromatic hydrocarbon residue or heterocyclic group is attached directly to the carboxyl group; or one formed by removing a hydroxy group from the carboxyl group of a substituted aliphatic carboxylic acid Wherein a straight- or branched-chain or cyclic saturated or unsaturated aliphatic carboxylic acid optionally containing oxygen or sulfur atom in its chain structure is linked with an aromatic hydrocarbon residue or heterocyclic group with or without oxygen or sulfur atom existing therebetween; wherein said aliphatic carboxylic acid is a straight- or branched-chain aliphatic acid having 1 to 10 carbon atoms and a cyclic aliphatic carboxylic acid having 6 to 8 carbon atoms, and said aromatic hydrocarbon residue is phenyl or naphthyl and said heterocyclic group is a monocyclic or polycyclic heterocyclic group containing 1 to 4 heteroatoms selected from the group consisting of oxygen, nitrogen and sulfur in its ring structure, the aliphatic moiety of said aliphatic carboxylic acid, said aromatic hydrocarbon residue and said heterocyclic group optionally having 1 to 3 substituents selected from the group consisting of halogen, hydroxyl, amino, nitro, cyano, sulfonic acid group, carboxyl, $C_1$–$C_6$ alkyl, $C_1$–$C_6$ alkoxy and $C_1$–$C_6$ alkoxyimino.

6. A process as defined in claim 1 wherein the acyl group represented by $R_3$ is 2-thienylacetyl, phenylacetyl, phenoxyacetyl, furylacetyl, pyridylacetyl, pyrimidylacetyl, oxazolylacetyl, oxadiazolylacetyl, thiazolylacetyl, thiadiazolylacetyl, triazolylacetyl, tetrazolylacetyl, 2-amino-thiazol-4-yl-acetyl, α-syn-methoxyimino-α-(2-amino-thiazol-4-yl)acetyl, {D(−)-α-(4-ethyl-2,3-dioxo-1-piperazinecarboxamide)-α-4-hydroxyphenyl}acetyl, {(Z)-2-(2-aminothiazol-4-yl)-2-(2-carboxypropyloxyimino)}acetyl, formyl, acetyl, propiony, tetrazolylthioacetyl, 4-pyridylthioacetyl, 4-pyridyloxyacetyl, benzolyl, p-nitrobenzolyl or 4-isoxazolylcarbonyl.

7. A process as defined in claim 1 wherein the solvent is an organic solvent or a mixture of an organic solvent and water.

8. A process as defined in claim 1 wherein the reaction is carried out in a solvent and in the presence of a base or metal salt which is used in an amount of about 0.5 to about 2 moles per mole of the compound of the formula (II), and the heterocyclic compound of the formula (III) is used in an amount of about 1 to about 10 moles per mole of the compound of the formula (II).

9. A process as defined in claim 8 wherein the solvent is an organic solvent or a mixture of an organic solvent and water.

10. A process as defined in claim 8 wherein the base or metal salt is alkali metal carbonate, alkaline earth metal carbonate, carbonate of copper group metal, oxide of copper group metal, alkaline earth metal oxide, oxide of zinc group metal, oxide of aluminum group metal, oxide of carbon group metal, oxide of iron group metal, hydroxide of copper group metal, organic amine or anion exchange resin.

11. A process as defined in claim 1 wherein the reaction is carried out at a temperature of about 20° to about 50° C.

* * * * *